United States Patent [19]
Bhatia et al.

[11] Patent Number: 5,405,015
[45] Date of Patent: Apr. 11, 1995

[54] SYSTEM AND METHOD FOR SEEKING AND PRESENTING AN AREA FOR READING WITH A VISION SYSTEM

[75] Inventors: Chandrakant R. Bhatia, Libertyville; Richard J. Kuhns, Crystal lake; Steven D. Vannice, Wheeling, all of Ill.; Michael E. Stober, Woodland Hills, Calif.

[73] Assignee: Videojet Systems International, Inc., Wood Dale, Ill.

[21] Appl. No.: 105,299

[22] Filed: Aug. 11, 1993

[51] Int. Cl.$^6$ .................................................. B07C 5/00
[52] U.S. Cl. ................................ 209/524; 250/223 B; 209/939; 209/526; 209/587
[58] Field of Search ................ 250/223 B, 223 R; 209/522, 524, 526, 528, 576, 577, 587, 938, 585, 529, 523

[56] References Cited

U.S. PATENT DOCUMENTS

| | | | |
|---|---|---|---|
| 3,327,849 | 6/1967 | Sorbie | 209/526 |
| 3,356,853 | 12/1967 | Rottmann | 209/526 X |
| 3,942,001 | 3/1976 | O'Connor . | |
| 4,025,202 | 5/1977 | Deane | 209/526 X |
| 4,209,802 | 6/1980 | Fogg et al. | 209/939 X |
| 4,230,266 | 10/1980 | Juvinall | 250/223 B |
| 4,620,090 | 10/1986 | Decloux . | |
| 4,636,635 | 1/1987 | Kronseder . | |
| 4,691,231 | 9/1987 | Fitzmorris | 209/526 X |
| 4,701,612 | 10/1987 | Sturgill | 209/526 X |
| 4,850,696 | 7/1989 | Yamato | 250/223 B |
| 4,855,608 | 8/1989 | Peterson, II . | |
| 4,967,070 | 10/1990 | Ringlien | 250/223 B |
| 5,064,043 | 11/1991 | Macdonald . | |
| 5,065,439 | 11/1991 | Takasaki et al. . | |
| 5,072,127 | 12/1991 | Cochran | 250/223 B |
| 5,111,516 | 5/1992 | Nakano et al. . | |
| 5,136,157 | 8/1992 | Apter et al. . | |
| 5,280,170 | 1/1994 | Baldwin | 250/223 B |
| 5,305,391 | 4/1994 | Gomibuchi | 250/223 B |

FOREIGN PATENT DOCUMENTS

| | | |
|---|---|---|
| 151059 | 7/1988 | European Pat. Off. . |
| 293510 | 7/1995 | European Pat. Off. . |

*Primary Examiner*—D. Glenn Dayoan
*Attorney, Agent, or Firm*—Leydig, Voit & Mayer, Ltd.

[57] ABSTRACT

A system for analyzing the physical condition of a moving article, such as a glass bottle, in a stream of articles of manufacture which are moving at a predetermined speed. A light source illuminates a portion of the moving article to be analyzed at an illumination angle, and a camera obtains an image of the illuminated portion of the article. The camera is disposed to view the article at a viewing angle that is distinct from the illumination angle, thereby substantially reducing the amount of reflected light received by the camera. A transparent surface is interposed between the camera and the article and angled to reduce the amount of reflected light received by the camera. A computer or the like processes the image to evaluate the physical condition of the article, and categorizes the article into distinct categories based upon the physical condition of the article.

32 Claims, 11 Drawing Sheets

SYSTEM AND METHOD FOR SEEKING AND PRESENTING AN AREA FOR READING WITH A VISION SYSTEM

FIELD OF THE INVENTION

The present invention relates generally to inspection equipment, and more particularly to a system and method for manipulating an article to present an area thereon for identification or visual inspection.

BACKGROUND OF THE INVENTION

In manufacturing environments, it is often desirable to identify articles of manufacture by reading a code imprinted or otherwise present on the article. It is also often desirable to inspect articles of manufacture for quality control purposes. In this manner, articles that are out-of-date, or that have defects, flaws and the like may then be rejected or otherwise distinguished from the lot of articles undergoing such inspection.

For example, in the bottling industry, returnable bottles that are over a certain age limit (such as those over four years old) may be automatically rejected regardless of their apparent condition. Similarly, bottles may be automatically rejected if a significant number of their lot have previously been detected as flawed.

Moreover, it is often desirable to inspect the physical condition of both glass and plastic bottles, such as inspecting for the presence of foreign matter or for cracks in the bottle. In the case of returnable plastic bottles, each time the bottles are handled, washed, pressurized, depressurized, and so on, the bottles are subjected to stress which may cause cracks to form thereon, particularly on their bottom portion.

One such bottle inspection system, which is directed to detecting foreign matter within a bottle, employs a camera above the bottle operating in conjunction with a light source below the bottle. However, such a system does not provide reliable data for analyzing the stress cracks on the bottom of the bottle. For example, with this typical arrangement, newer bottles create a significant amount of glare which makes it difficult to detect stress cracking on the bottles. Moreover, such data is even more unreliable if water droplets are present in the area being analyzed. In short, these typical bottle inspection systems are unreliable and therefore unsuitable for performing proper stress cracking inspections.

However, properly inspecting the condition of the bottles for defects such as cracks and other flaws and reading the codes on the bottles is a time consuming and expensive process. Since returned bottles are randomly mixed and since each bottle generally experiences an unpredictably different amount of stress during its useful life, each bottle must be individually inspected to achieve any measure of assurance that the bottle is acceptable for refilling.

Ordinarily, at the time of manufacturing each bottle receives an ink or laser-imprinted coded label i.e., code string, that is used to identify the bottle during its useful life. In this manner, information regarding the bottle's date of manufacture, place of manufacture, lot number, and the like may be imprinted thereon. In the case of returnable plastic bottles, the coded label is often imprinted on the lower portion of the bottle perpendicular to its longitudinal axis. However, it is difficult to consistently position these coded labels on the bottles. For example, as the bottles move along a conveyer belt, they often become slanted upwards or downwards, i.e., they often become slightly nonperpendicular to the longitudinal axis of the bottle. During the application of the code string, when a bottle is slightly skewed, the code string is necessarily imprinted thereon in a similarly skewed manner.

Moreover, the bottles are often randomly rotated about their longitudinal axes both initially during the labeling process and later during subsequent handling. When attempting to read the code at a later time, such as when the bottles are placed upon a conveyor belt to be ultimately filled, it is often difficult to locate the positions of the labels while they are moving. This is particularly true when the conveyor belt is at maximum capacity, i.e., when there is essentially no gap between the bottles on the conveyor belt.

Adding to the complexity of locating and reading the code is the fact that the bottles are continuously moving and it is usually undesirable to reduce the throughput of the system by reducing the average speed of the bottles or the conveyor belt to facilitate the reading and inspection of the articles. Likewise, inspection of the bottles is also a difficult procedure due to their continuous movement.

OBJECTS AND SUMMARY OF THE INVENTION

Accordingly, it is an object of the present invention to provide a method and apparatus for sensing the article with a fixed sensing system without altering the average speed or throughput of the bottles.

Yet another object is to provide a method and apparatus for temporarily halting the movement of an article in order to manipulate its rotational orientation for seeking and presenting a specific area thereon for sensing.

It is a related object to individually accelerate each article relative to the average speed of articles prior to sensing to provide sufficient time to halt and rotate each article for visual identification.

Another object of the invention is to provide a method and apparatus as characterized above that provides sufficient time to inspect the article and determine its physical condition or obtain other visual analysis of the article.

Yet another object of the invention is to provide a system and method for identifying bottles with a vision system regardless of the angle of the identifying label thereon relative to the longitudinal axis of the bottle.

A further object of the invention is to provide a method and apparatus of the above kind that categorizes bottles based on the result of the identification or the inspection.

Yet another object of the present invention is to provide a method and apparatus for inspecting the physical condition of a bottle in a manner that provides accurate and reliable data at conventional conveyor speeds.

Another object is to provide a method and apparatus of the above kind that obtains visual data with a significantly reduced amount of glare.

Still another object is to provide a method and apparatus for rejecting articles as a result of the identification or the inspection.

Briefly, the invention provides a system and method for seeking and sensing a specific area on articles in a stream of articles of manufacture which are moving at a predetermined speed. An article, such as a bottle moving along a conveyor belt, is accelerated relative to a predetermined speed of the other bottles on the conveyor belt. As the bottle approaches the sensing station, the bottle is separated from the other bottles due to its acceleration. The bottle is then halted at the sensing station where the bottle is manipulated, if necessary, to locate and present a selected area on the halted bottle to a sensing device. When the article is halted and the selected area is in view of the sensing device, the article is then sensed and information corresponding to the selected area is obtained. After being sensed, the article is again accelerated and resumes its previous speed, thereby maintaining the throughput of the system. Such a sensing device may include a vision system capable of obtaining video images of the article and a video processor capable of analyzing the electronic representation of the obtained image.

An advantage of the present invention includes the ability to manipulate and sense an article in a stream of articles while the article is halted and stationary without losing throughput of the entire system. High quality images and analysis of the articles which were heretofore unavailable are now readily obtainable by using the system or method of the present invention.

In an alternate embodiment directed to evaluating stress cracks without halting the bottles, a camera is mounted below the moving bottles at a viewing angle relative to the perpendicular axis of the bottles. A light source, also mounted below the bottles, illuminates the bottom portion of each bottle to assist the camera in sensing a clear image of the bottles. By mounting the camera at a viewing angle distinct from the illumination angle of the light source, the amount of glare from the light source is significantly reduced. In addition, the distinct angle helps reduce the glare caused by water droplets which may be present within the bottles. The camera and light source are located below a glass surface, which is also angled relative to the camera and light source to further reduce undesirable glare. In this alternate embodiment, at the point of sensing by the camera, the bottles are conveyed over a pair of parallel rails so that the image is obtainable from below. A mask is preferably arranged to block a portion of the obtained image which is not being analyzed, thereby blocking and further reducing undesirable glare.

Other objects and advantages will become apparent from the following detailed description when taken in conjunction with attached drawings. Moreover, while the invention is susceptible of various modifications and alternative constructions, certain illustrated embodiments thereof have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the invention.

DETAILED DESCRIPTION OF THE PREFERRED EMBODIMENT

Figure 9:
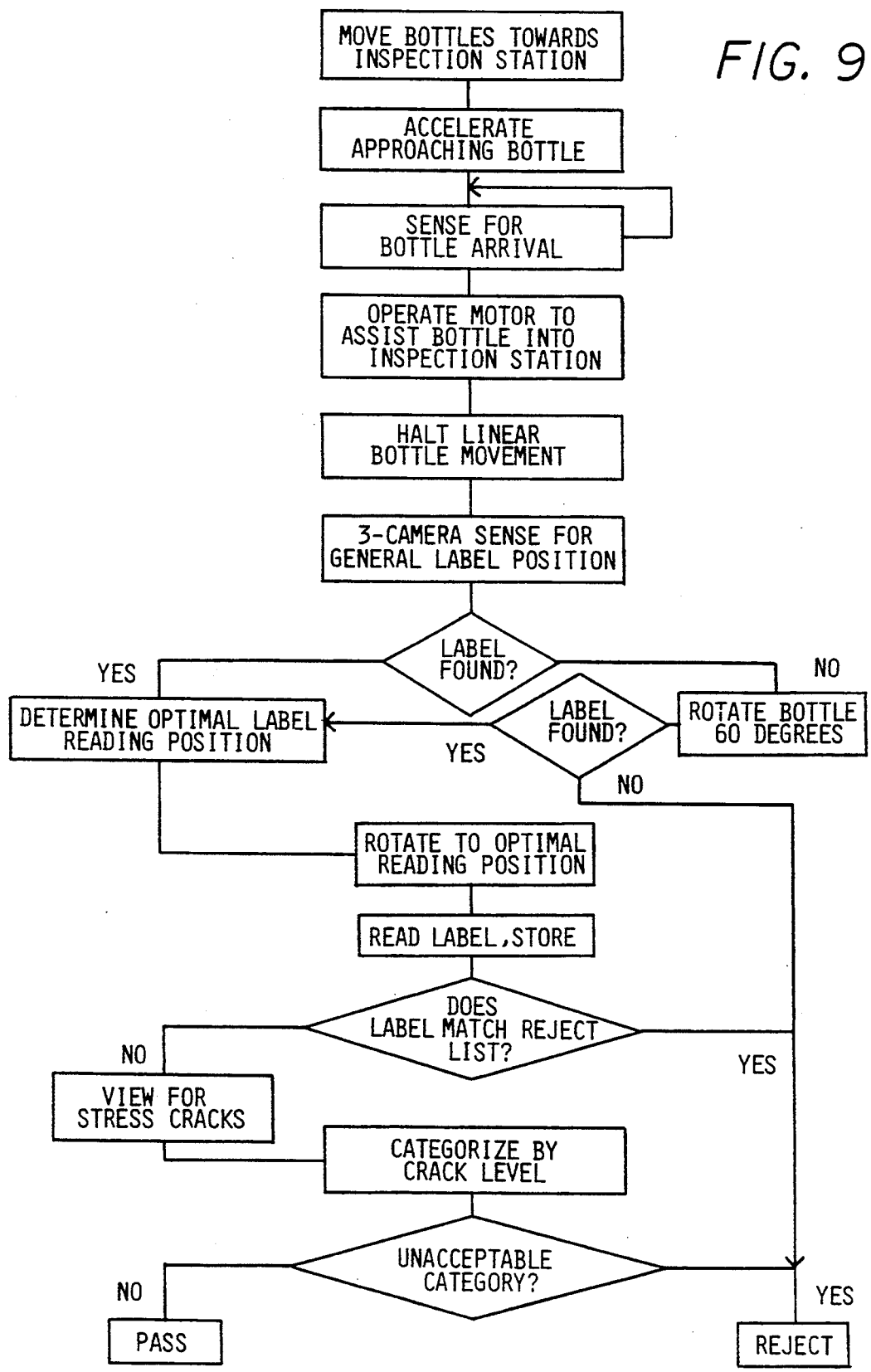
FIG. 9 is a flow chart representing the general flow of a bottle through the system shown in FIG. 1.

Referring to FIGS. 1-4 of the drawings and the steps shown in FIG. 9, there is shown a preferred embodiment of the present invention in the form of an inspection system 20 having a transporting system including a conveyor belt system 22 for moving articles of manufacture such as bottles 24 toward a sensing station 26. The bottles 24 are transported primarily in one linear direction in the illustrated embodiment as represented by directional arrows 28.

Figure 2:
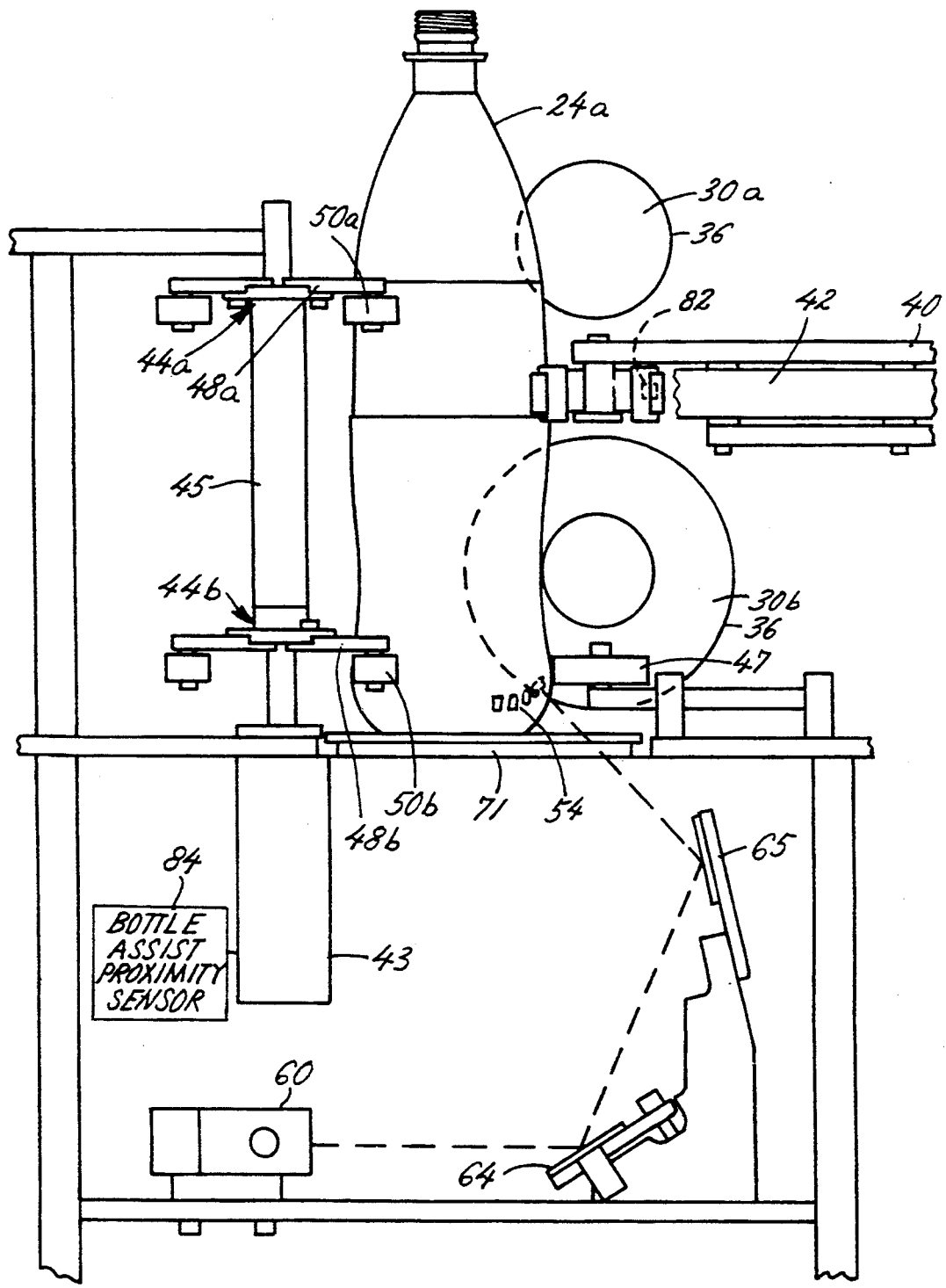
FIG. 2 is a side view of the embodiment shown in FIG. 1 illustrating a bottle halted in the sensing station for optical sensing of a code string on the bottle.

The transporting system of the present invention further includes an article accelerator/separator means, lead screw 30, threaded on its input side 32 with a thread 36 of increasing width in the direction of movement of the bottles, arrow 28. The lead screw 30 is rotated at a speed corresponding to the speed of the conveyor belt 22 such that the start of the thread 36 is able to accept the next bottle in the stream at the input side 32 of the lead screw 30, provided one is present. In other words, the lead screw 30 is rotated so that the bottles 24 will not stack up at the input side 32. The bottles 24 are carried between the ridges of the thread 36 and are also held against a rail 38. It can be readily appreciated that instead of utilizing a single lead screw for separating the bottles, an upper lead screw 30a and a lower lead screw 30b may be employed as shown in FIG. 2. In this manner, bottles are provided with greater stability, particularly if the bottles are empty.

Figure 1:
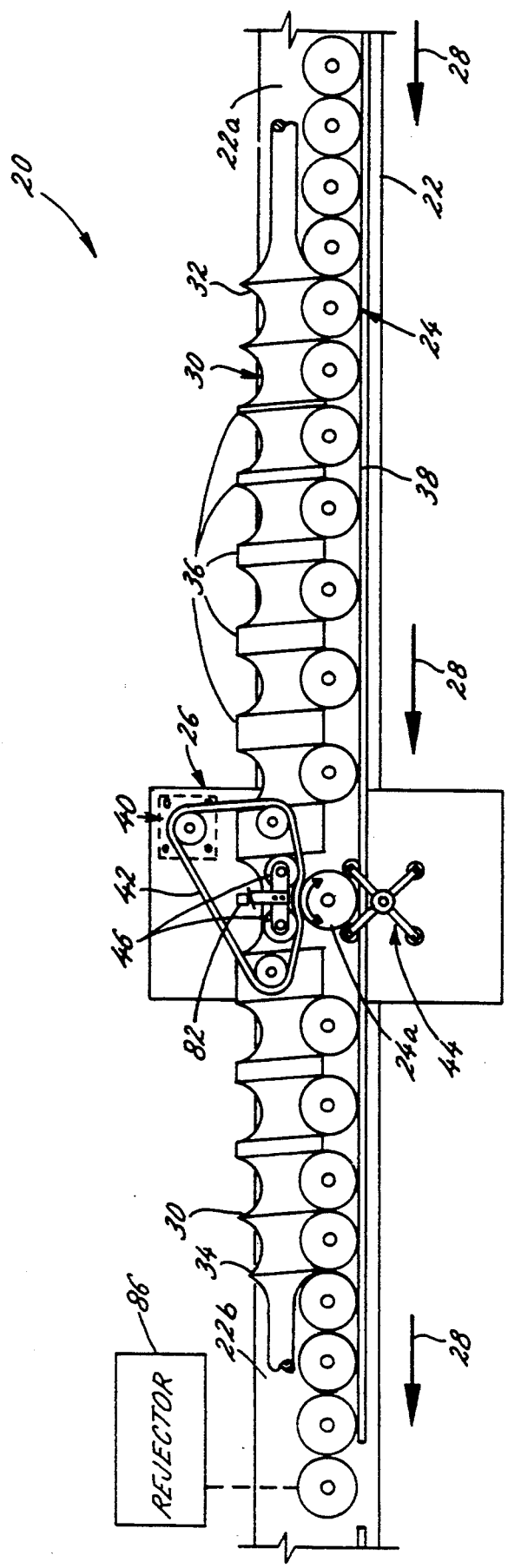
FIG. 1 is a top view of a preferred embodiment of the present invention, in the form of an inspection system, illustrating the general flow of bottles through a sensing station.

In the embodiment shown in FIG. 1, a dual conveyor belt system 22 is employed having a first conveyor belt 22a for feeding bottles 24 towards the lead screw 30 and a second conveyor belt 22b for transporting bottles 24 away from the lead screw 30. Alternatively, a conveyor system having a single conveyor belt may be arranged to travel beneath a fixed, smooth surface once the lead screw 30 has control of the bottle so that the bottle can freely slide thereon. Indeed, virtually any transporting system is sufficient provided that the surface beneath the sensing station 26 is transparent to allow for visual reading of the bottle as described in detail below. One such conveyor and lead screw system is commercially available from CSS International Corporation, Philadelphia, Pennsylvania.

Assuming for reasons of simplicity that a single lead screw 30 is employed, since the spiralling input thread 36 of the lead screw 30 increases in lateral width away from the input side 32, the bottles 24, which are carried between the ridges of the thread 36, are accelerated relative to their speed on the conveyor 22. In other words, the bottles 24 on the input side 32 become separated by a greater distance as they travel further away from the input side 32 of the lead screw 30 due to the increasing lateral width of the thread 36 therebetween.

In accordance with one aspect of the invention, after a bottle is sufficiently accelerated it is halted for a period of time at the sensing station 26, while the system still maintains an overall average velocity essentially equal to the velocity of the conveyor belt 22. During the time that each article is halted, the article is sensed or further manipulated to locate a particular area to be sensed. In the embodiment of FIG. 1, the bottle being sensed, bottle 24a, is rotated to find a particular area having a coded label for optically reading with a fixed vision system as described in more detail below. Nevertheless, other sensing means such as magnetic, X-ray, sonar, contact sensing, and the like may alternatively be utilized depending on the nature of the article and the type of inspection required. Similarly, further manipulation of the article including elevation, tilting, and the like may be performed on the article depending on the type of inspection required.

To halt the article for manipulation in the embodiment shown in FIG. 1, a star wheel 44 is employed to capture the bottle as it enters a gap in the thread of the lead screw 30. The star wheel 44 is driven by an indexing device 43, such as a ratchet or Geneva movement, which is mechanically coupled to the lead screw 30. The lead screw 30 indexes in 90 degree increments and allows the bottle 24a to remain in the sensing area for 270 degrees ($\frac{3}{4}$) of a rotation of the lead screw. One such indexing device is commercially available from Cyclo Index Inc., Carthage Missouri.

Although not necessary to the invention, similar to the dual (upper 30a and lower 30b) lead screw arrangement, it can be readily appreciated that a dual star wheel arrangement comprising upper star wheel 44a and lower star wheel 44b (FIG. 2) is preferable for certain applications. In the embodiment shown in FIG. 2, the indexing movement of the multiple star wheel 44 is kept in synchronization by connecting both star wheels 44a and 44b together on a common shaft 45.

As the lead screw rotation begins to cause the star wheel 44 to index to its next position, the movement of the star wheel 44 activates a bottle-assist-proximity-sensor 84 which provides a signal to a processor board 88a of a vision system 88 (FIG. 4) which includes a processor and memory. Preferably, the signals to and from the processor board 88a are first buffered through a suitable input-output interface, i.e., vision system I/O 88b, which may be included on the processor board 88a, or may be separate from the processor board but internal to the vision system 88, or even an external interface such as one including optoelectronic isolators. At an appropriate moment after the signal from the bottle-assist-proximity-sensor 84 is detected by the vision system 88, the vision system processor board 88a outputs a signal to activate and control a motor 40, generally through a motor drive means 41. In the embodiment shown, the motor 40 is a stepping motor operated in accordance with pulses enabled by or supplied from the vision system processor 88a, however it can be appreciated that a properly controlled servomotor will similarly provide the desired movement.

The motor 40 is arranged to rotate a drive belt 42 that is disposed and tensioned to contact the bottle 24a. Accordingly, to pull the bottle into the star wheel arms and ultimately the sensing station 26, the motor 40 is controlled to operate the drive belt 42 in a clockwise manner as considered in the orientation of the system of FIG. 1.

Since the operation of the star wheel 44 is dependent on the rotation of the lead screw 30, and since the movement of the wheel 44 triggers the initial operation of the drive belt 42, the indexing movement of the star wheel 44 is synchronized with the arrival of a bottle such that an appropriate pair of its arms are open to accept a bottle at the moment that a bottle is present. The operation of the drive belt 42 assists the bottle into the arms of the star wheel 44, and the wheel 44 continues its indexing movement in conjunction with the drive belt 42 to guide the bottle 24a into the sensing position of FIG. 1. The movement of the star wheel 44 then ceases for the next 270 degrees of the revolution of the lead screw 30, during which time the sensing operations are performed before the next bottle arrives. After sensing, the bottle 24a is removed from the sensing station 26 in a similar manner by the operation of the drive belt 42 and star wheel 44 which feed the bottle 24a into the lead screw 30 in the direction of the exit side 34. Ordinarily, this is accomplished simultaneously with the loading of the subsequent bottle into the sensing station 26 as described above.

Once the bottle is in proper position for sensing, in the illustrated embodiment the bottle 24a is sensed to optically read an identifying label (such as a code string 54) printed on a particular area of the bottle, ordinarily on the side of the bottle near the bottom. However, as mentioned above, the bottles are typically randomly rotated when they enter the sensing station 26, and accordingly, to more readily read the code string 54, the bottle 24a is rotated, if necessary, to align the code string 54 with one of the sensing cameras 60, 61 or 62 (shown in FIG. 8). Thus, when the bottle 24a is within the inspection area, the drive belt 42 is controllably operated to manipulate (i.e., rotate) the bottle 24a for reading.

To enable the manipulation, the arms 48a and 48b (shown in FIG. 2) of the star wheel 44 which hold the bottle in place are provided with rollers, 50a and 50b respectively, so that the bottle can freely be rotated by drive belt 42. Lower rollers 47 (see FIG. 2) are also provided opposite the lower star wheel rollers 50b to ensure that the bottle remains at the proper vertical orientation.

To prevent the drive belt 42 from slipping, the belt 42 is pressed against the bottle 24a by a pair of rollers 46. The rollers 46 are preferably pressed against the inner surface of the belt by spring tension. The spring tension further eases the entry and the exit of the bottle to and from the sensing station. It can be readily appreciated that the spring constant can be varied in dependence on the characteristics of the bottles. For example, the spring tension may be lower for empty plastic bottles than for full glass bottles, thereby ensuring that the empty plastic bottles are not collapsed by an overly powerful spring force and that the heavier bottles do not slip on the drive belt 42 due to an insufficient spring force.

In any case, the outer surface of the bottle 24a forces the rollers 46 back, compressing the tensioning spring slightly and triggering a bottle-ready-sensor 82 which detects when a bottle is present and which provides a signal corresponding thereto. The signal from the bottle-ready-sensor 82 notifies the vision system processor board 88a to stop the motor 40 driving belt 42 and to activate the sensing.

Figure 8:
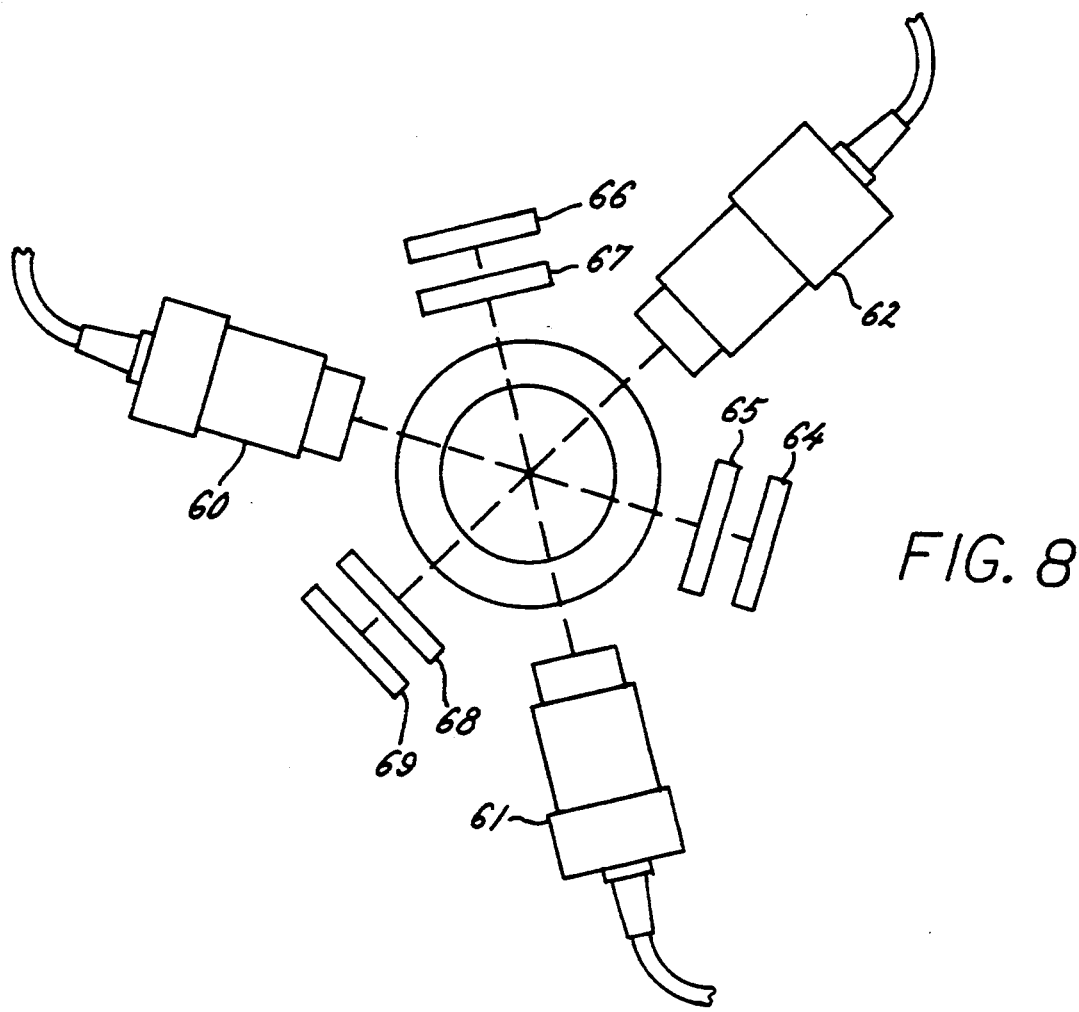
FIG. 8 is a top view of the embodiment shown in FIG. 1 showing the relative positioning of the label reading cameras and mirrors.

In accordance with one aspect of the present invention, as shown in FIG. 8, in order to sense the bottle 24a to read the area having its printed code string 54, the provided vision system 88 comprises three CCD (charge coupled device) cameras 60-62 which are arranged to view the bottle 24a at 120 degree intervals. The vision system 88 operates the drive belt 42 in conjunction with the image obtained to locate the code string 54. First, while the bottle 24a is halted, an image is obtained from each of the three cameras 60-62 and fed to a frame splitter board 88c present within the vision system 88. The frame splitter board 88c combines (i.e., multiplexes) in real-time the three video signals into a single video signal wherein the upper, center and lower portions of the image correspond to the individual images from the three cameras. The single video output signal is then passed as a video input to a camera board 88d, which digitizes the image (from eight-bit digitized analog information) into a one bit per pixel representation. It should be noted that at this time, the processor board 88a has directed the camera board 88d to select as its input the output of the frame splitter board 88c (as opposed to the signal output by camera 72 described hereinbelow).

Due to the arcuate nature of the surface of the bottle 24a and the desire to have the cameras 60-62 resolve a clear image of the code string 54, each of the three cameras 60-62 scans a sixty degree field for a total of 180 degrees scanned (one-half the circumference of the bottle). Mirrors 64-69 are provided in pairs with each camera to reflect the images of the bottle 24a into the cameras 60-62 so that the cameras can be placed at a convenient location for reasons of space, camera protection, maintenance and so on. As best shown in FIGS. 2 and 8, each of the cameras 60-62 and mirrors 64-69 are disposed beneath the bottle, and thus it can be appreciated that in the embodiment shown, the bottle-under-inspection 24a is supported in the sensing station 26 on a transparent glass surface 71 to allow the cameras to obtain the proper images.

After the images are obtained by the cameras 60-62, the camera board 88d provides the digitized output to a signature board 88e. The camera board 88d maintains the cameras 60-62 and 72 synchronized by providing a camera synchronization information signal. The signature board 88e converts the digitized video to a list of X and Y coordinates for the obtained image based on matches with patterns previously identified. For example, the previously identified pattern for this image scan might be a four-by-four group of dark pixels; each group of four that correlates has its X and Y coordinates added to the list. Depending on the application, a different correlation pattern may be preprogrammed into the system for matching with the obtained image prior to every digitized camera shot provided by the camera board 88d.

Figure 4:
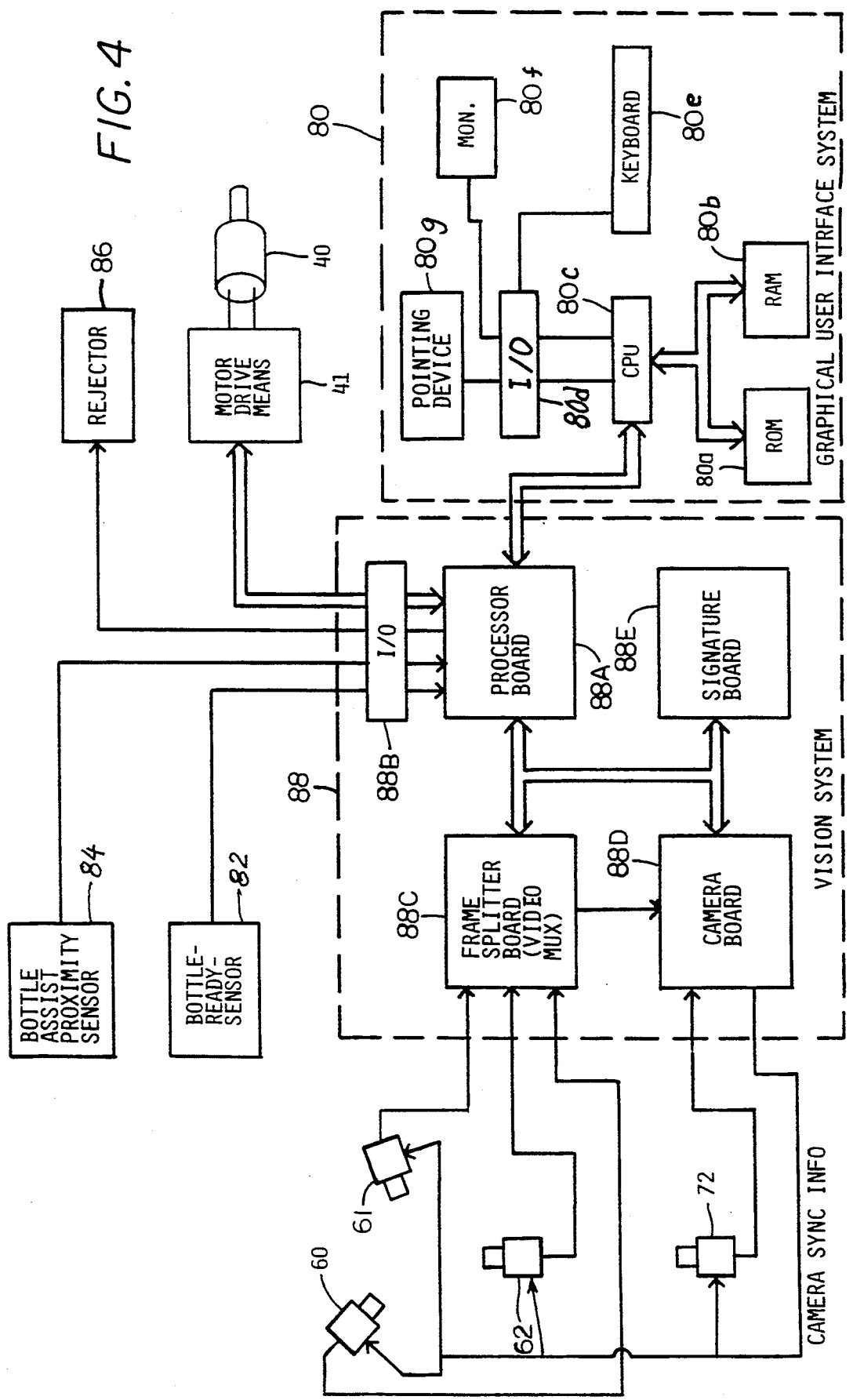
FIG. 4 is a block diagram of a control and vision system and user interface suitable for controlling the inspection system shown in FIG. 1.
Figure 13:
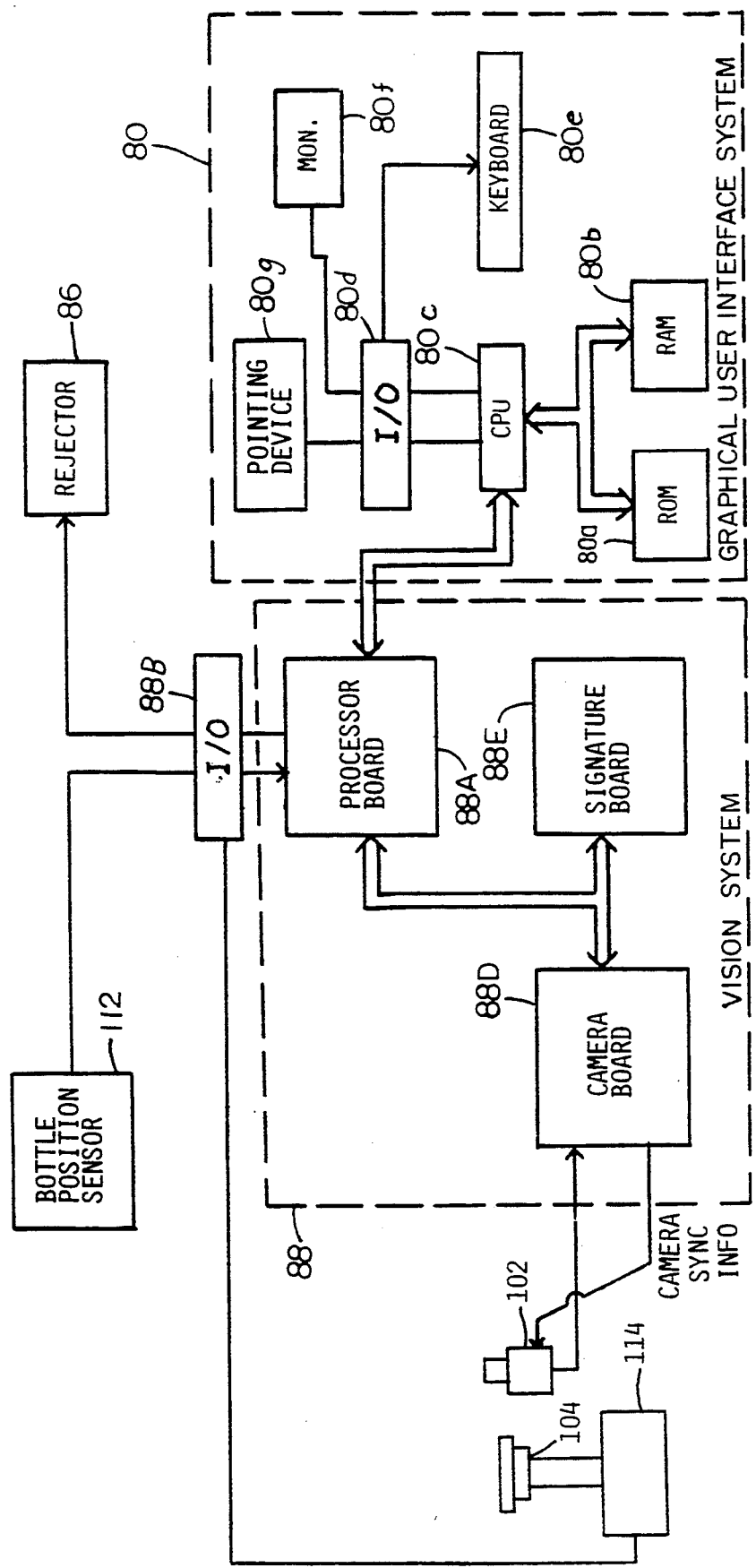
FIG. 13 is a block diagram of a control and vision system and user interface suitable for controlling the inspection system shown in FIG. 10.

The vision system 88 is a Ramvision hardware system 88 comprising Ramvision system boards (Ramvision Inc., Chatsworth, California), including the frame splitter board #810406, Processor Board #800100A, Camera Board #810403C, Signature Board #800105B and a Mother Board #800110A. In addition, as shown in FIGS. 4 and 13, the Ramvision System is connected to a graphical user interface system 80, typically configured as a microcomputer system including a memory means such as a ROM 80a and a RAM 80b, processing means such as a Central Processing Unit 80c, Input-/Output (I/O) means 80d including input means such as a keyboard 80e, display means such as a monitor 80f and pointing device (i.e., mouse) 80g. This graphical user interface system 80 allows the input of various parameters to the Ramvision system 88, for example, the preprogrammed pattern of pixels that is matched during an image scan when the signature board assembles a coordinate list.

Once the coordinate list has been obtained, the vision system processor board 88a analyzes the coordinate list in the signature board's (88e) memory to determine if any part of the printed code 54 has been detected. If the multiplexed image contains no part of the code 54, then the system assumes that the code 54 is present on the other half of the bottle 24a which has not yet been scanned. Should this occur, the vision system processor board 88a instructs the motor 40 to operate the belt 42 to rotate the bottle 24a sixty degrees. In this manner, the full 360 degree circumference of the bottle 24a is scanned, if necessary. Of course, since a code or label generally occupies at least a few degrees, it is feasible to rotate the bottle less than sixty degrees and still locate a part of the label, if one is present.

Regardless of whether the code string 54 is immediately located or located after a sixty degree adjustment, once the code string 54 is located, the vision system processor board 88a determines how much the bottle 24a needs to be rotated to ensure that the code string 54 is at the optimal viewing angle for reading by one of the cameras 60-62. Depending upon the position of the code string 54 within the image obtained, the vision system processor board 88a directs the motor 40 to operate the belt 42 to rotate the bottle 24a and achieve the optimal viewing angle of the code string 54, e.g., in the center of the area viewed by one of the cameras 60-62. In the embodiment shown, the vision system processor board 88a provides the number of pulses to the motor 40 which are necessary to step the motor 40 to the desired angle in the proper rotational direction.

Once the optimal angle is reached, the vision system processor board 88a directs the appropriate camera (based on the whether the label was detected within the upper, center or lower portion of the image, as determined by the label's Y-coordinate) to obtain an electronic image of the bottle area including the now-centered code string 54. In the unlikely event that a bottle does not contain a label, the bottle can be rejected or otherwise identified as flawed as described hereinbelow. Thus, for purposes of simplicity herein, it is assumed that every bottle in the stream contains a proper label.

As shown in the steps of FIG. 9, once the label has been determined to be within view of one of the cameras 60-62, the processor on the vision system processor board 88a determines the location of the label by evaluating the video information obtained from that camera. The vision system processor board 88a then determines an optimal location for reading the identifying label, i.e., the processor therein calculates how many steps (left or right) that the motor needs to take to rotate the bottle so that the label is centered in the field of view. This step is generally referred to as a "seek and center" step.

Figure 5:
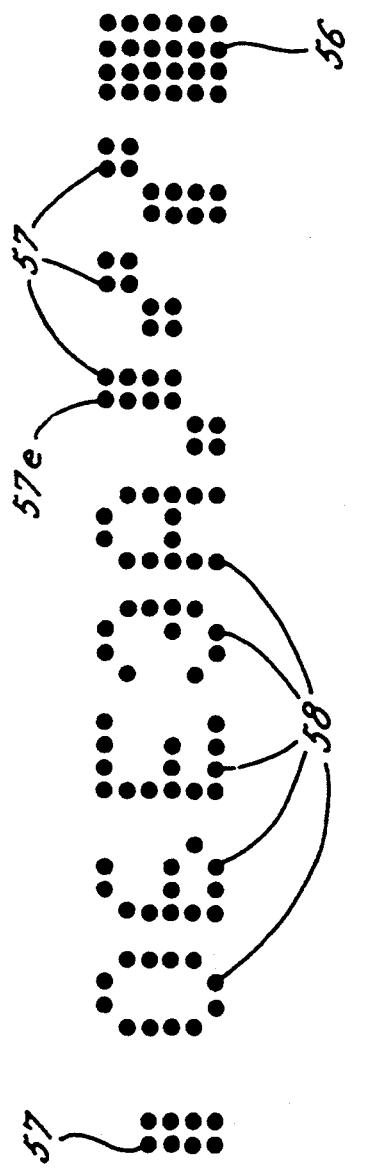
FIG. 5 is an enlarged representation of a code string.

In the embodiment shown in FIG. 5, the identifying label comprises a code string 54 demarcated by leading and trailing standards known as fiducials 55, 56. These fiducials 55, 56 are preferably solid box-shaped dot matrix characters. Once the optimally centered image is obtained, the positions of the fiducials 55, 56 are analyzed by the Ramvision hardware vision system 88 to determine the image coordinates of the four outermost corners of the code string 54. This is accomplished by performing a filtered search through the list of matching coordinates provided by the signature board 88e. With this information, the vision system processor board 88a is able to compensate for any skewing of the label relative to the horizontal axis by determining where the characters comprising the code string 54 are within the image stored in memory. For example, a code string that angles upwardly to the right will have the coordinates of its rightmost character vertically higher within the stored image than the coordinates of its leftmost character. To properly read the code string, the vision system processor board 88a compensates for this skew angle by utilizing the slope of the code string 54 in a trigonometric operation to determine the coordinates corresponding to the characters 57, 58 between the fiducials 55, 56.

Once the amount of skew is determined, the characters in the code string 54 are decoded by the vision system processor board 88a. Although such code strings contain both binary characters 57 and human readable characters 58, the embodiment shown analyzes only the binary characters 57 for reading the code string 54. Nevertheless, it is alternatively feasible to read the human readable characters 58, although such a procedure is not necessary and may ordinarily take substantially more analysis.

Figure 6:
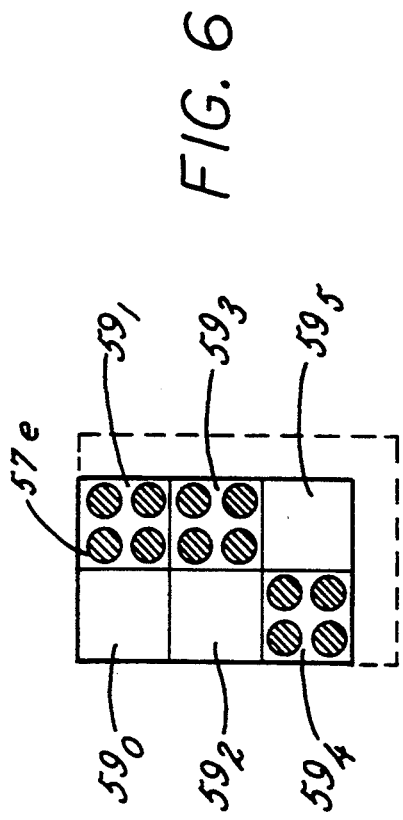
FIG. 6 is an enlarged representation of a binary character within a code string.

As shown in FIGS. 5 and 6, when initially imprinted on the bottle, the characters of the code string 54 are arranged in a five-by-seven dot matrix of which four-by-six of the possible dot locations are used to form the characters of the fiducials 55, 56, and the binary characters 57.

To read the binary characters, the vision system processor 88a first creates a map of the code string outline based on the outermost coordinates, compensating for any skew as described above. The vision system processor board 88a next analyzes the coordinates of each 4-by-6 binary dot pattern, or box, to determine the locations of each of the binary characters 57. Each box is subsequently divided into a number of zones corresponding to the number of bits that make up the binary character. For example, as shown in FIG. 6, in a the code string 54, the binary characters are made up of six bits in a three row, two column matrix. Accordingly, the box drawn around this character consists of six zones 590-595 (three high and two across), each zone housing up to four printed dots.

At this time, the processor board 88a groups the matches that fall within the areas mapped for each character. If the number of coordinate matches falling within a zone exceed a threshold count, the zone is considered a one-bit. It should be noted that the number of memory location bits, or pixels, depends on the resolution of the cameras 60–62, and does not necessarily equal the number of printed dots. Since dust, scratches, imperfections in the characters, tolerances in determining the skew angle, and so on might make an occasional memory location pixel appear to be the opposite of what it actually is, a threshold counting system is employed. In this system, if the number of pixel matches exceeds the threshold number (for example, if greater than fifty percent of the total pixels are determined to be matches in that zone) then that zone in the box is considered to be a one bit.

Once a six zone box has been converted into a bit pattern of ones and zeroes, the system can determine the ASCII value of the binary characters 57. The bits of each character make up a six-bit word that corresponds to a letter between A–Z inclusive or a number between 0–9 inclusive. In the illustrated embodiment, there are five such binary characters in the code string, although any number of characters which is sufficient for identification purposes is acceptable. For example, each binary character 57 corresponds to a human readable character 58 in the string "06E3A" wherein the "06" might represent the day, the "E" might represent the month, the "3" the year in the decade, and the "A" the plant code. Regardless of the actual number and meaning of the characters in the string, the code string 54 is then known to the system and can be further utilized.

For example, if the vision system processor 88a reads and decodes a code string that has been previously entered into a reject list, a simple comparison is performed and the system rejects the article containing that code. Similarly, it should be appreciated by those skilled in the art that the code strings can be recorded or grouped for statistical purposes or manipulated like any other data.

While the bottle is present in the sensing station 26, it may also be desirable to inspect the physical condition of the bottle 24a. In the embodiment shown, the bottom of the bottle may be viewed for stress cracks. It can also be appreciated that other types of inspections can be performed while the article is halted depending on the nature and testing needs of the article.

Figure 3:
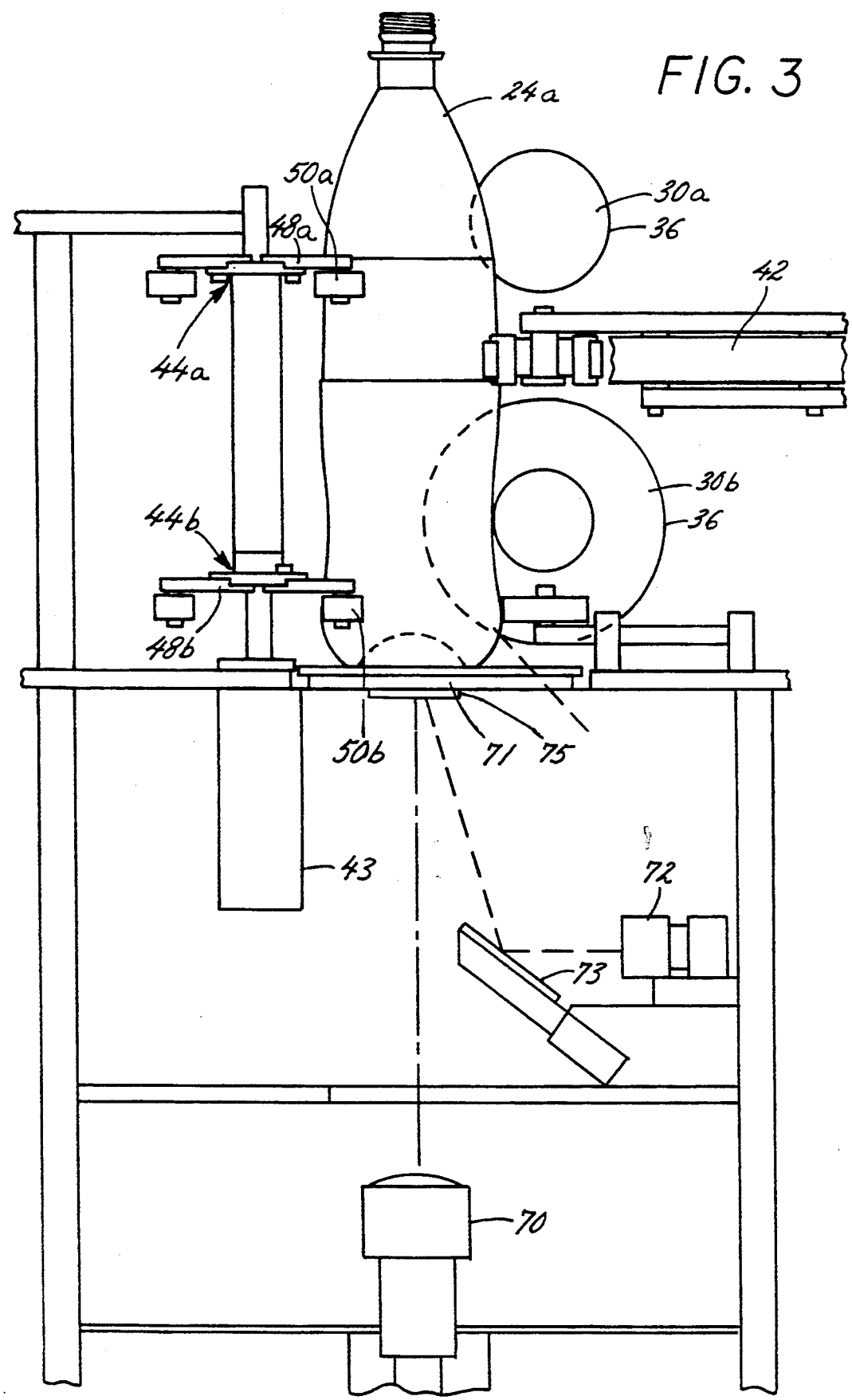
FIG. 3 is a side view of the embodiment shown in FIG. 1 illustrating a bottle halted in the sensing station for optical inspection of the bottom portion of the bottle.

As shown in FIG. 3, to sense the bottom of the bottle for stress cracks, the bottle-under-inspection 24a is supported in the sensing station 26 on a transparent glass surface 71 and illuminated from below by a light source 70. A fourth camera 72 and optional mirror 73 are employed to obtain the image of the bottle bottom. Because only a small area of the bottom of these types of bottles actually contacts a resting surface during normal use, it is generally not necessary to scan the entire bottom of the bottle 24a but only the general area of contact. In addition, the illumination of cracks within the bottom of the bottle is visually enhanced by reducing reflected glare. As a result, in the embodiment shown, a circular darkening mask 75 is placed beneath the bottle such that the light source only illuminates the contact area that is desired to be analyzed.

Figure 7:
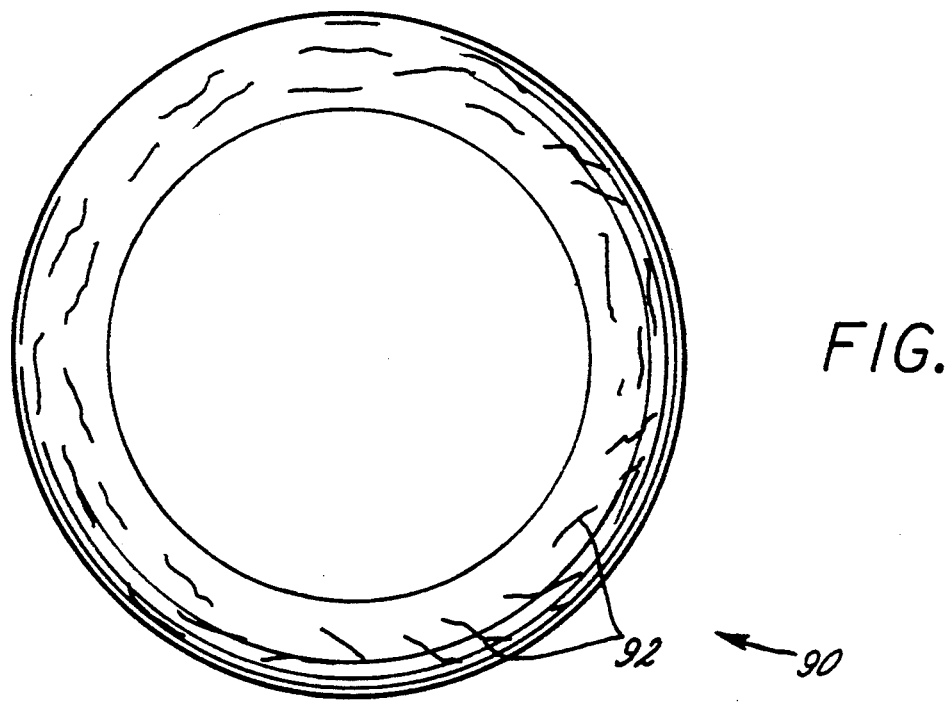
FIG. 7 is a representation of the image obtained for measuring the crack density of a bottle's lower surface.

As shown in FIG. 7, the camera 72 thus obtains a ring-like image 90 within the entire image obtained, and feeds it through the camera board 88d to the signature board 88e. During this part of the analysis, the processor board 88a directs the camera board 88d to input an image from the camera 72, (as opposed to from splitter board 88c as described hereinbefore). The stress cracks 92 generally appear as dark striations against a light background within the ring-like image 90. Thus, the image is enhanced so that only the gray level of actual cracking is evaluated, while higher intensity white levels due to glare are omitted. To determine the severity of the stress cracks, i.e. the stress crack density, the ring-like image 92 is inspected by comparing the area of the ring-like FIG. 92 against a four pixel-by-four pixel pattern, i.e., template. Any area where the template fits is considered a match.

The number of matches are subsequently summed together by the signature board 88e to obtain a number which is indicative of the total crack density of the bottle. The bottle is categorized based on the number obtained for each bottle. Generally, bottles having too high a number are rejected, while bottles having a lesser number are passed through the station.

For example, in the embodiment shown, the bottles are classified into four levels or categories of cracking, with the highest (worst) level being rejected and the others being allowed to pass. Additionally, since each code string and corresponding numbers are known, the system can record the information for later statistical analysis. Of course, bottles may be classified into any number of different categories on an application-by-application basis.

After all of the sensing is complete, i.e., an image of the stress cracks has been obtained and the code string has been read, the code string for the just-sensed bottle is compared against a list of such code strings to determine if the bottle should be rejected. The list is organized as a reject list, such that bottles having code strings that match code strings on the list are rejected. In addition, the actual code strings may be compared against a range of codes, against a date, and so on depending on the desired rejection criteria. Additionally, more complex sorting procedures may be utilized to sort bottles according to certain predetermined characteristics instead of employing a simple accept or reject procedure. Moreover, it is possible to reject a bottle based on its code string without further inspecting it for stress cracks or vice versa, and if both are analyzed the analysis may be performed in any order.

When the sensing is complete, the bottle 24a is removed from the sensing station 26 by rotating the star wheel 44 in conjunction with the belt 42. Again, the motorized belt 42 is operated by the vision system processor 88a to assist the indexing star wheel 44, ordinarily at the same time that the next bottle in the stream is being moved into the inspection station 26. As the just-sensed bottle 24a exits the inspection station 26, the bottle 24a is fed to the exit side 34 of the lead screw 30. Bottle 24a is then decelerated so that the bottles are recombined in same manner and at their same original speed, i.e., the speed of the conveyor system 22.

Regardless of the cause for rejecting a particular bottle, to reject a bottle identified as belonging to a reject category, a rejector 86 is provided for removing the bottle after it leaves the inspection station 26. In the embodiment shown, the rejector 86 comprises an electromagnetic solenoid arranged to topple a bottle at an appropriate gap in the rail 38, i.e., at a reject gate, so that a bottle identified for rejection is removed from the main conveyor system 22. However, since the bottles are rejected, if at all, after they exit the lead screw 30, the vision system processor 88a does not generate a signal to operate the reject actuation until the bottle exits the lead screw and is at the appropriate location (i.e., at the reject gate) to ensure that the proper bottle is rejected. (Note that during this delay time, any remaining part of the image processing may still be occurring since the vision system processor 88a is not overly burdened by the bottle removing/loading and bottle accepting/rejecting operations. Such a feature allows a greater bottle throughput.) To calculate the proper amount of delay, the number of revolutions of the lead screw may be counted to determine when to actuate the rejector 86 for each rejected bottle. For example, after each revolution of the lead screw the vision system processor 88a may determine whether the bottle currently at the rejector 86 had been previously identified for rejection. Of course, it can be appreciated to those skilled in the art that an appropriate delay can be generated in numerous ways.

Once the data for the bottle has been obtained, it is preferably recorded and displayed at the graphical user interface 80. For example, the data may be recorded for statisical analysis, and graphically displayed in chart form.

Figure 10:
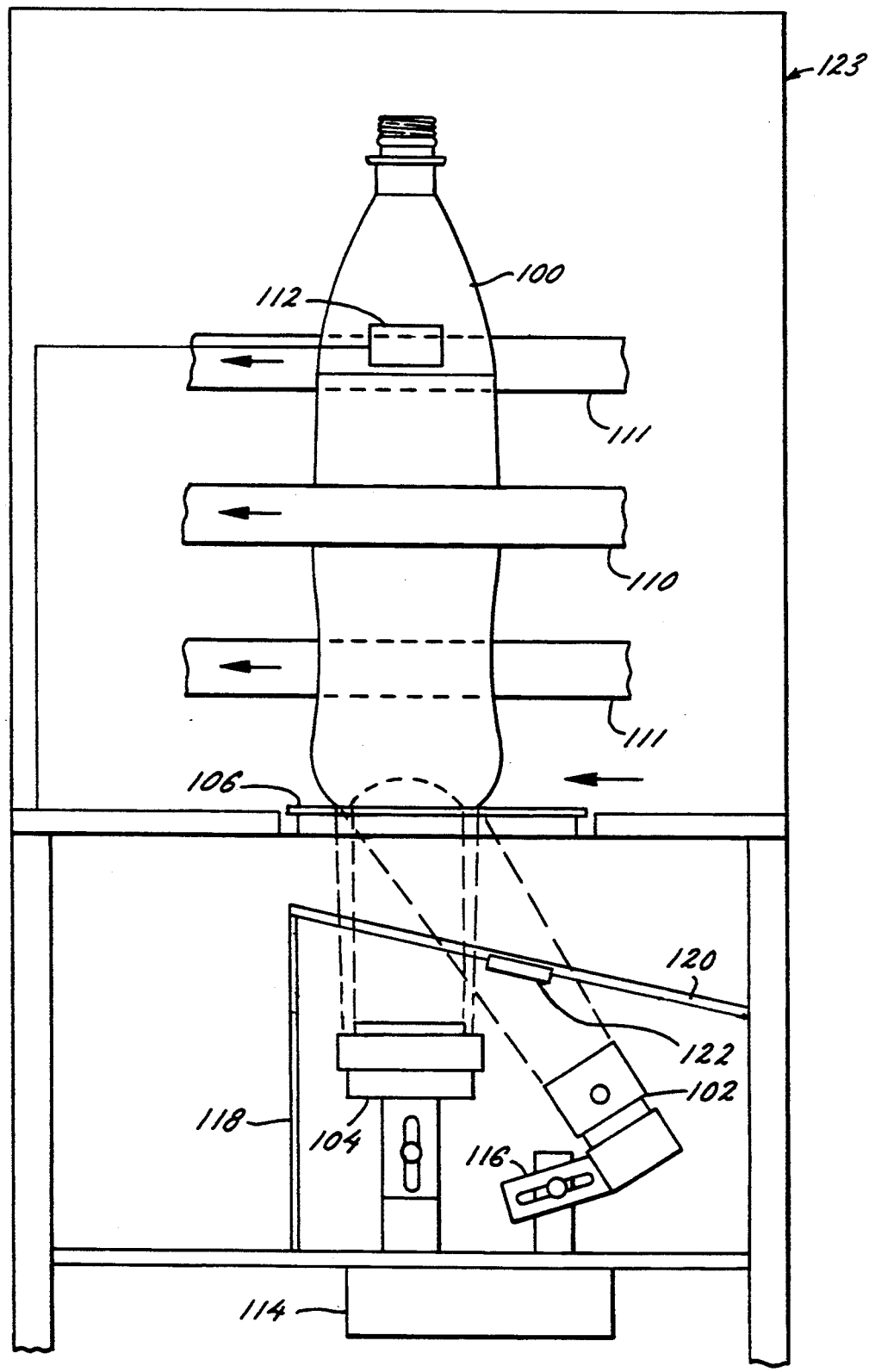
FIG. 10 is a side elevational view of an alternate embodiment for inspecting the stress cracking on bottles in motion.
Figure 11:
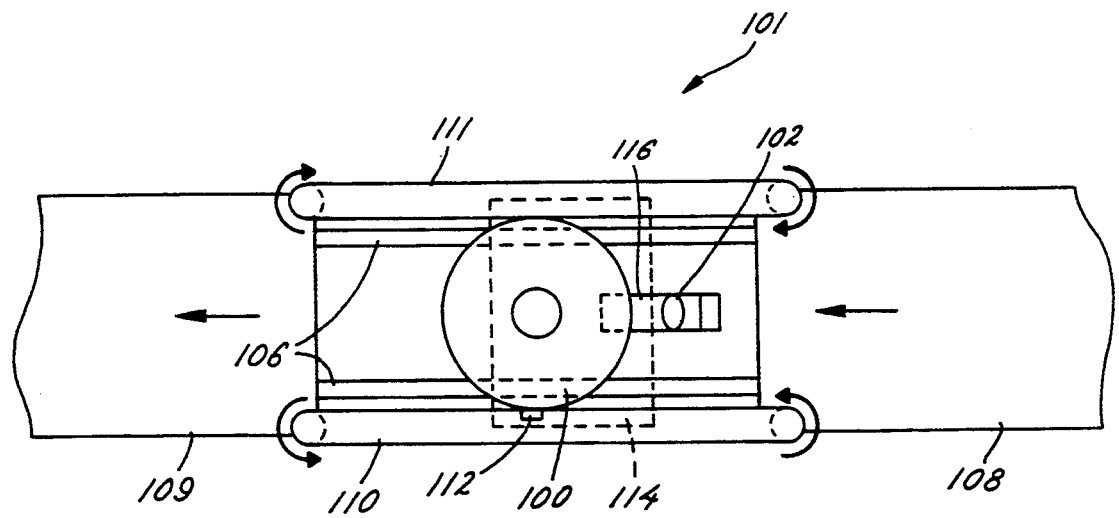
FIG. 11 is a top view of FIG. 10.

In an alternate embodiment directed to detecting levels of stress cracks in continuously moving bottles, without stopping their movement, a bottle 100 is transported past a high-speed camera 102 and a strobe light source 104 which are disposed beneath the bottle 100, as shown in FIGS. 10 and 11. As the bottles enter the inspection station 101 from the conveyor 108, a pair of spaced apart, generally parallel rails 106 are provided to support the bottles. The rails 106 are open to below and provide the camera 102 with view of bottom of the moving bottle 100. In this manner, a stream of bottles may be inspected for stress cracking without halting the linear conveyance thereof.

Although not necessary to the invention, to assist in transporting the bottle 100 across the rails 106, a set of three drive belts including a single front belt 110 and two rear belts 111 (as viewed in the orientation of FIG. 10) are provided to grip the bottle 100. These belts 110, 111 are operatively connected to the main conveyor belt drive so that they move at the same speed as conveyor belts 108 and 109. As viewed from above as in FIG. 11, the rear belts 111 are driven in a clockwise manner while the front belt 110 is driven counterclockwise so that the opposite insides of the belts move the bottle (or stream of bottles) appropriately.

Referring to FIG. 13, there is shown a control and vision system, similar to the control and vision system shown in FIG. 4, which is suitable for operating the inspection system shown in FIG. 10. Identically referenced numerals in FIG. 10 correspond to identically referenced components of FIG. 4 and function similarly. As a result, the operation of the control and vision system and the operation of the identically referenced components shown in FIG. 10 are very similar to the operation of those shown in FIG. 4, except where herein noted.

As the bottle enters the inspection station 101, a bottle-position sensor 112 (preferably an ultrasonic sensor available from Hyde Park Corp., model #SM553A-000) detects the position of the bottle 100 and signals the vision system processor 88a that the bottle is in the appropriate position to obtain an image of the bottle (i.e. that the bottle is in the field of view of camera). The vision system processor board 88a then signals the strobe 114 to actuate the light source 104, thereby illuminating the bottom portion of the bottle 100 for a short duration. While the bottle 100 is illuminated, the camera 102 obtains an image of the bottom portion of the bottle 100 and feeds said image to the vision system 88 as described above. In the embodiment shown, the light source 104 comprises a fiber optic ring which is actuated by the strobe 114, and which may be of the type available from EG&G Corp. Of course, it is also feasible to operate a continuous light source and obtain the image only at the appropriate instant.

In accordance with one aspect of the invention, the camera 102 is positioned at a viewing angle distinct from the illumination angle of the light source 104. Although not required, the viewing angle of the camera 102 is preferably angled between 15 and 45 degrees from the perpendicular axis of the bottle 24a; an angle of approximately 30 degrees is shown in FIG. 10. To this end, the camera 102 is held in place by a support 116. By shining the light source 104 at an angle substantially normal to the bottom portion of the bottle while obtaining the image at a different angle, the amount of glare reflecting into the camera 102 is minimized, thus reducing the effects of light reflected from the bottle 100 and the effects of water droplets in the bottle. A significantly more reliable inspection image is thereby obtained.

Figure 14:
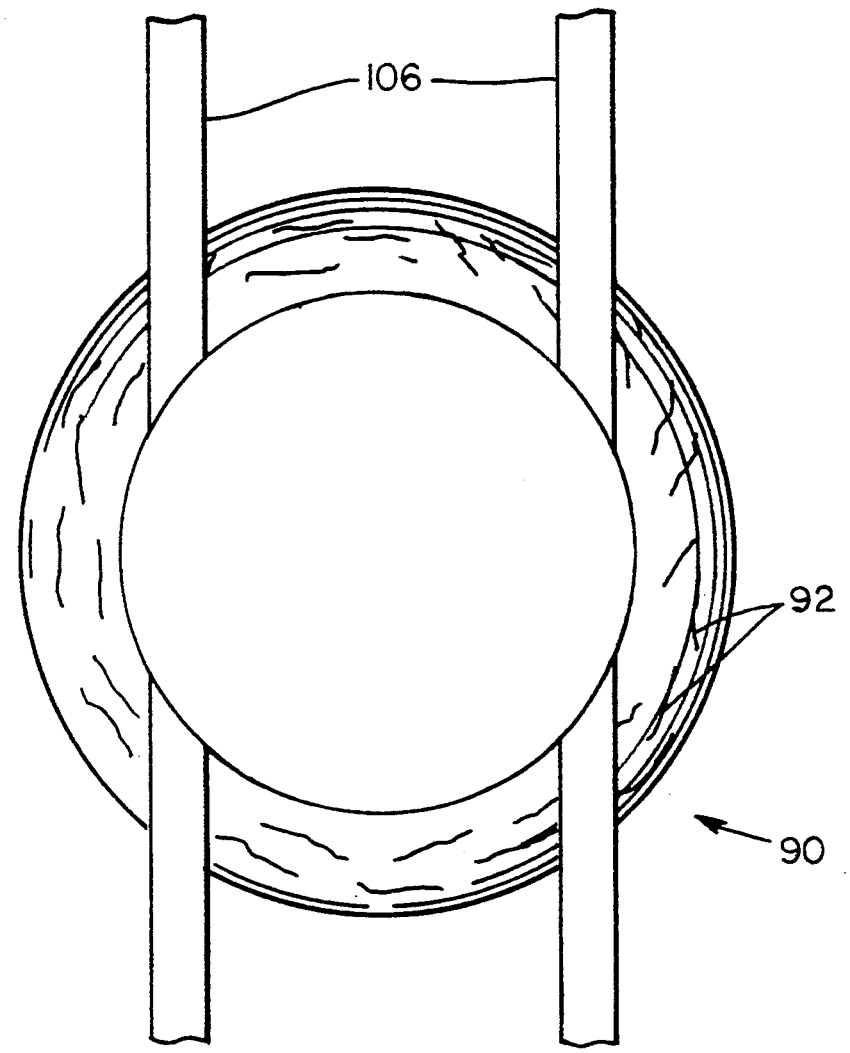
FIG. 14 is a representation of the image obtained by the embodiment shown in FIG. 10 for measuring the crack density of a bottle's lower surface.

To protect the camera 102 and light source 104, an enclosure 118 having a transparent upper surface 120 is provided. In keeping with the invention, the transparent surface 120 of the enclosure 118 is also angled to reduce glare. Although not required, the surface 120 is preferably angled between 5 and 15 degrees from horizontal; an angle of approximately 10 degrees is shown in FIG. 10. As an added feature, the angling of the surface 120 further prevents significant amounts of water and or dust from accumulating thereon. To further reduce glare, a mask 122 is disposed between the camera and the bottle to mask out a portion of the bottle such that only a ring-shaped image of the bottom of the bottle 100 is obtained, as shown in FIG. 14.

Preferably, the mask 122 is dimensioned and positioned to block from the view of the camera 102 the center one-third area of the bottom of the bottle 100. To reduce or eliminate ambient light which might generate erroneous stress cracking data, the entire inspection operation is performed within an opaque cover 123.

As explained above, to obtain the image the bottle-position sensor 112 triggers the strobe 114 (preferably through the vision system processor board 88a) and an image of the unmasked area is acquired by the camera 102. As shown in FIG. 14, the rails block certain portions of the bottom of the bottle 100 from the view of the camera 102. This is of little consequence, however, because the stress cracking of a bottle is usually uniform throughout the circumference of the bottom of the bottle. Alternatively, a glass surface (such as glass surface 71 shown in FIGS. 2 and 3) may be employed to present the entire image area to the camera 104.

By processing the video image and counting the dark pixels as described hereinbefore, the relative density of stress cracking is determined, since the degree of stress cracking is proportional to the number of dark pixels detected. Once the degree of stress cracking is obtained, the bottle can be systematically categorized as described above. For example, threshold levels may be set at the graphical user interface 80 by a system operator to sort the bottles into one of four categories and a display (such as monitor 80f) may be provided to indicate the category status of the bottles being inspected.

Figure 12:
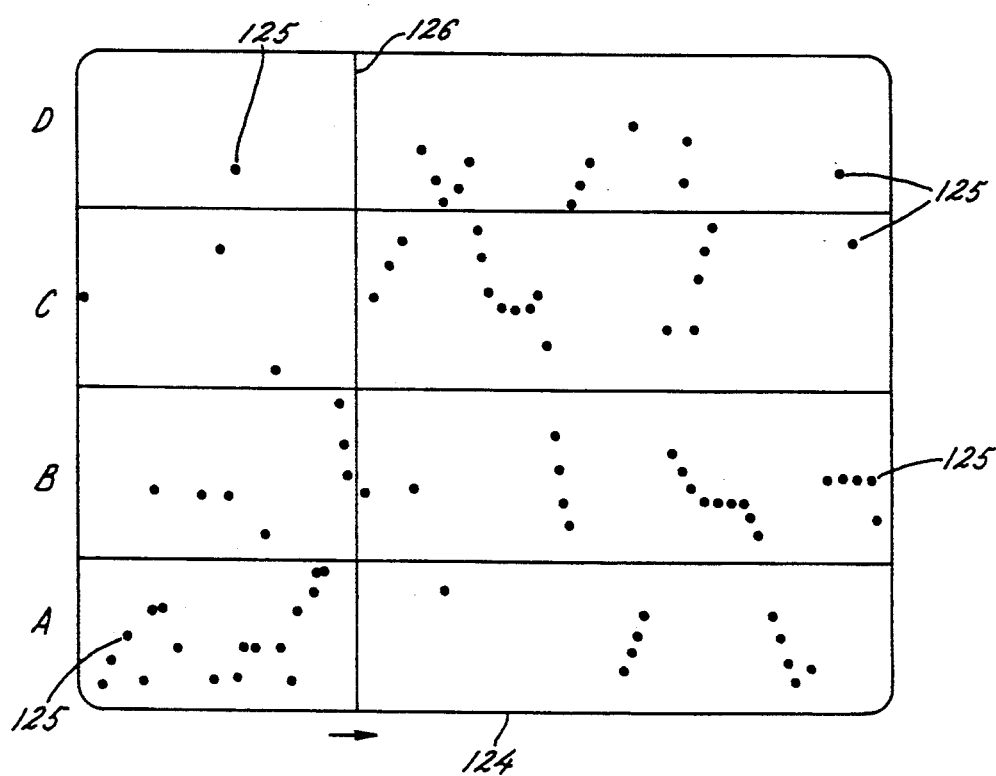
FIG. 12 is a representation of a graphical screen displaying data corresponding to levels of stress cracking in bottles.

In the alternate embodiment above, as shown in FIG. 12, a real-time graphical display 124 of the most recently categorized one-hundred bottles is provided in a histogram form on the monitor 80f. Dots 125 are placed on the screen to represent the cracking level of a bottle relative to the four categories A-D. A vertical cursor 126 sweeps across the monitor 80f from left to right to update the display 124 with the most recently obtained bottle data. As it sweeps, the cursor overwrites the old bottle data and continuously displays bottle data from the most current one-hundred bottles inspected. Of course, other suitable monitoring stations known to those skilled in the art may also be employed.

As can be seen from the foregoing, a method and system has been provided for temporarily halting an article for sensing with a fixed sensing system without altering its average speed. While halted, the article's rotational orientation may be manipulated for seeking and presenting a specific area thereon for sensing. A sufficient amount of time is available for manipulation and inspection due to the initial acceleration of each article entering the sensing station relative to the average speed of articles prior to sensing.

The sensing of the article includes visual identification by reading a label thereon, and inspection of the article for determining its physical condition, or other visual analysis. In an alternate embodiment, the physical condition of the articles may be inspected without halting the articles during the inspection, thereby maintaining the average speed of the articles.

Once the article has been identified and inspected, the articles may be categorized based on the visual information obtained. Articles in certain categories may also be rejected from others evaluated.

What is claimed is:

1. A system for analyzing the physical condition of a moving article in a stream of articles of manufacture which are moving at a predetermined speed, comprising:

a light source for illuminating the bottom of the moving article to be analyzed, the light source disposed to transmit light at an illumination angle that is substantially normal to the bottom of the article;

a camera for obtaining an image of the bottom of the article, the camera disposed to view the bottom of the article at a viewing angle that is distinct from the illumination angle, thereby substantially reducing the amount of reflected light received by the camera with the image; and means for processing the image to evaluate the physical condition of the article, including means for categorizing the article into distinct categories based upon the physical condition of the article.

2. The system of claim 1 wherein the camera and light source are housed in an enclosure, said enclosure having an upper surface substantially transparent to visible light for obtaining an image therethrough, the upper surface being angled to further reduce the amount of reflected light received by the camera.

3. The system of claim 2 further comprising an opaque cover which surrounds the article and blocks ambient light from illuminating the article.

4. The system of claim 1 further comprising a display device operatively connected to the processor means for providing a display representative of the physical condition of the article.

5. The system of claim 2 wherein the article is a bottle and the physical condition analyzed is the amount of stress cracking on the bottom portion of the bottle, and wherein the camera and light source are disposed below the bottle to analyze the amount of stress cracking on the bottom portion of the bottle.

6. The system of claim 5 wherein a mask is disposed between the camera and the bottle such that a ring-shaped image of the bottom portion of the bottle is obtained.

7. The system of claim 5 further comprising position sensing means for detecting when the position of the bottle is within the field of view of the camera.

8. The system of claim 1 wherein the article is a bottle and the light source is disposed to radiate light through the bottom of the bottle towards the top of the bottle and the camera is disposed such that the viewing angle is between fifteen and forty-five degrees from the illumination angle.

9. The system of claim 1 wherein the article is a bottle and the camera obtains only a single image of the bottom of the bottle, and wherein the means for processing the image evaluates the stress cracking in the bottle from only the single image.

10. A system for analyzing the physical condition of a moving article in a stream of articles of manufacture which are moving at a predetermined speed, comprising:
   a light source for illuminating a portion of the moving article to be analyzed, the light source disposed to transmit light on the portion of the moving article at an illumination angle;
   a camera for obtaining an image of the portion of the article, the camera disposed to view the article at a viewing angle that is distinct from the illumination angle, thereby substantially reducing the amount of reflected light received by the camera with the image;
   means for processing the image to evaluate the physical condition of the article, including means for categorizing the article into distinct categories based upon the physical condition of the article; and
   an enclosure for housing the camera and light source, said enclosure having an upper surface substantially transparent to visible light for obtaining an image therethrough and being angled to further reduce the amount of reflected light received by the camera.

11. The system of claim 10 further comprising an opaque cover which surrounds the article and blocks ambient light from illuminating the article.

12. The system of claim 10 wherein the article is a bottle and the physical condition analyzed is the amount of stress cracking on the bottom portion of the bottle, and wherein the camera and light source are disposed below the bottle to analyze the amount of stress cracking on the bottom portion of the bottle.

13. The system of claim 12 wherein a mask is disposed between the camera and the bottle such that a ring-shaped image of the bottom portion of the bottle is obtained.

14. The system of claim 12 further comprising position sensing means for detecting when the position of the bottle is within the field of view of the camera.

15. The system of claim 14 wherein the light source comprises a strobe light operatively connected to the position sensing means such that the position sensing means operates the strobe light to momentarily illuminate the moving bottle when the position sensing means detects the bottle within the field of view of the camera.

16. The system of claim 12 wherein the light source is disposed to transmit light at an angle substantially normal to the bottom of the bottle and the camera is disposed such that the viewing angle is between fifteen and forty-five degrees from the perpendicular axis of the bottle.

17. The system of claim 16 wherein the transparent upper surface is angled between five and fifteen degrees with respect to the bottom of the bottle.

18. The system of claim 10 further comprising a display device operatively connected to the processor means for providing a display representative of the physical condition of the article.

19. The system of claim 10 wherein the enclosure includes at least two sides for supporting said upper surface.

20. The system of claim 10 further comprising means for rejecting articles within a specific category.

21. A system for analyzing the physical condition of a moving article in a stream of articles of manufacture which are moving at a predetermined speed, comprising:
   a light source for illuminating a portion of the moving article to be analyzed, the light source disposed to transmit light on the portion of the moving article at an illumination angle;
   a camera for obtaining an image of the portion of the article, the camera disposed to view the article at a viewing angle that is distinct from the illumination angle, thereby substantially reducing the amount of reflected light received by the camera with the image;
   a surface interposed between the camera and the article, the surface substantially transparent to visible light for obtaining an image therethrough and being angled to reduce the amount of reflected light received by the camera; and
   means for processing the image to evaluate the physical condition of the article, including means for categorizing the article into distinct categories based upon the physical condition of the article.

22. The system of claim 21 wherein the light source and camera are both disposed substantially below the article and wherein the transparent surface is further interposed between the light source and the article.

23. The system of claim 22 further comprising an opaque cover which surrounds the article and blocks ambient light from illuminating the article.

24. The system of claim 22 further comprising means for supporting the surface thereby forming an enclosure having the light source and the camera housed therein.

25. The system of claim 21 further comprising means for rejecting articles within a specific category.

26. The system of claim 21 further comprising a display device operatively connected to the processor means for providing a display representative of the physical condition of the article.

27. The system of claim 21 wherein the article is a bottle and the physical condition analyzed is the amount of stress cracking on the bottom portion of the bottle, and wherein the camera and light source are disposed below the bottle to analyze the amount of stress cracking on the bottom portion of the bottle.

28. The system of claim 27 wherein a mask is disposed between the camera and the bottle such that a ring-shaped image of the bottom portion of the bottle is obtained.

29. The system of claim 27 further comprising position sensing means for detecting when the position of the bottle is within the field of view of the camera.

30. The system of claim 29 wherein the light source comprises a strobe light operatively connected to the position sensing means such that the position sensing means operates the strobe light to momentarily illuminate the moving bottle when the position sensing means detects the bottle within the field of view of the camera.

31. The system of claim 27 wherein the light source is disposed to transmit light at an angle substantially normal to the bottom of the bottle and the camera is disposed such that the viewing angle thereof is between fifteen and forty-five degrees from the perpendicular axis of the bottle.

32. The system of claim 31 wherein the transparent upper surface is angled between five and fifteen degrees with respect to the bottom of the bottle.

* * * * *